(12) United States Patent
Kulas et al.

(10) Patent No.: US 9,232,952 B2
(45) Date of Patent: Jan. 12, 2016

(54) SURGICAL BUR WITH NON-PAIRED FLUTES

(75) Inventors: John W. Kulas, Euless, TX (US); Donald E. Stearns, Hico, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 724 days.

(21) Appl. No.: 13/447,372

(22) Filed: Apr. 16, 2012

(65) Prior Publication Data

US 2013/0274779 A1 Oct. 17, 2013

(51) Int. Cl.
*A61B 17/00* (2006.01)
*A61B 17/16* (2006.01)

(52) U.S. Cl.
CPC .................. *A61B 17/1615* (2013.01)

(58) Field of Classification Search
CPC . A61B 17/16; A61B 17/1615; A61B 17/1617
USPC ..................... 606/79, 80; 408/227
See application file for complete search history.

(56) References Cited

U.S. PATENT DOCUMENTS

| | | |
|---|---|---|
| 372,400 A | 11/1887 | Browne |
| 533,573 A | 2/1895 | Wilkens |
| 2,795,979 A | 7/1954 | Zerwick |
| 2,847,885 A | 8/1956 | Wagner |
| 3,872,594 A | 3/1975 | Gerteisen |
| 3,937,222 A | 2/1976 | Banko |
| 4,445,509 A | 5/1984 | Auth |
| 4,594,034 A * | 6/1986 | Maier ........................ 408/230 |
| 4,600,006 A | 7/1986 | Baker |
| 4,699,550 A | 10/1987 | Baker |
| 4,740,121 A | 4/1988 | Arnold |
| 4,803,982 A | 2/1989 | Baker |
| 4,830,000 A | 5/1989 | Shutt |
| 4,951,690 A | 8/1990 | Baker |
| 4,978,350 A | 12/1990 | Wagenknecht |
| 5,007,911 A | 4/1991 | Baker |
| 5,122,134 A | 6/1992 | Borzone et al. |

(Continued)

FOREIGN PATENT DOCUMENTS

| | | |
|---|---|---|
| DE | 19826276 | 12/1998 |
| JP | H06155126 A | 6/1994 |

(Continued)

OTHER PUBLICATIONS

International Search Report and Written Opinion mailed Aug. 28, 2013 for PCT/US2013/036269, claiming priority to U.S. Appl. No. 13/447,372, filed Apr. 16, 2012.

(Continued)

*Primary Examiner* — Kevin T Truong
*Assistant Examiner* — Si Ming Ku
(74) *Attorney, Agent, or Firm* — Harness, Dickey

(57) ABSTRACT

A surgical dissection tool for cutting bone and other tissue includes a cutting head having an outer surface having non-paired or an odd number of flutes formed therein. Each flute includes a rake surface intersecting with the outer surface to form a cutting edge, and a relief surface opposite the rake surface. The relief surface and the rake surface form a first angle. Each flute also includes a leading angled surface extending from the relief surface to a distal end portion of the cutting head, the leading angled surface and the rake surface forming a second angle substantially the same as the first angle.

15 Claims, 8 Drawing Sheets

(56) References Cited

U.S. PATENT DOCUMENTS

| | | | |
|---|---|---|---|
| 5,143,490 A | 9/1992 | Kopras | |
| 5,190,548 A | 3/1993 | Davis | |
| 5,236,291 A | 8/1993 | Agapiou | |
| 5,302,059 A | 4/1994 | Fabiano | |
| 5,429,504 A | 7/1995 | Peltier | |
| 5,514,141 A | 5/1996 | Prizzi, Jr. | |
| 5,575,650 A | 11/1996 | Niznick | |
| 5,579,185 A | 11/1996 | Tsai | |
| D378,780 S | 4/1997 | Shuler | |
| 5,618,293 A | 4/1997 | Sample | |
| 5,658,305 A | 8/1997 | Baker | |
| 5,810,517 A | 9/1998 | Bostic | |
| 5,833,402 A | 11/1998 | Martin | |
| 5,846,035 A | 12/1998 | Karafillis | |
| 5,855,581 A | 1/1999 | Koblish | |
| 5,913,867 A | 6/1999 | Dion | |
| 5,980,525 A | 11/1999 | Bryant | |
| 6,068,632 A | 5/2000 | Carchidi | |
| 6,132,448 A | 10/2000 | Perez | |
| 6,238,398 B1 | 5/2001 | Lechot | |
| 6,258,093 B1 | 7/2001 | Edwards et al. | |
| 6,332,886 B1 | 12/2001 | Green | |
| 6,431,801 B2 | 8/2002 | Vasudeva | |
| 6,435,780 B1 * | 8/2002 | Flynn | 407/53 |
| 6,511,493 B1 | 1/2003 | Moutafis | |
| 6,514,258 B1 | 2/2003 | Brown | |
| 6,547,495 B2 | 4/2003 | Meece et al. | |
| 6,562,046 B2 | 5/2003 | Sasso | |
| 6,579,298 B1 | 6/2003 | Bruneau | |
| 6,783,533 B2 | 8/2004 | Green | |
| 7,862,263 B2 | 1/2011 | Van Iperen | |
| 2004/0057803 A1 * | 3/2004 | Walrath | 407/54 |
| 2005/0203526 A1 | 9/2005 | Ellis | |
| 2005/0273107 A1 | 12/2005 | Stevens | |
| 2005/0283160 A1 | 12/2005 | Knisely et al. | |
| 2006/0085005 A1 | 4/2006 | Kenealy, III et al. | |
| 2006/0142775 A1 | 6/2006 | Heneberry et al. | |
| 2007/0010822 A1 | 1/2007 | Zalenski | |
| 2007/0213736 A1 | 9/2007 | Ducharme | |
| 2007/0280792 A1 | 12/2007 | Kochan | |
| 2008/0132929 A1 | 6/2008 | O'Sullivan et al. | |
| 2008/0167653 A1 | 7/2008 | Watlington | |
| 2008/0177294 A1 | 7/2008 | O'Neil | |
| 2008/0193234 A1 | 8/2008 | Davancens | |
| 2008/0215148 A1 | 9/2008 | Lesinski | |
| 2009/0023988 A1 | 1/2009 | Korner | |
| 2009/0024129 A1 | 1/2009 | Gordon | |
| 2009/0048602 A1 | 2/2009 | O'Donoghue | |
| 2009/0138015 A1 | 5/2009 | Conner | |
| 2009/0216235 A1 | 8/2009 | Ellis | |
| 2009/0222009 A1 | 9/2009 | Ellis | |
| 2009/0264888 A1 | 10/2009 | Neumeyer | |
| 2010/0054884 A1 | 3/2010 | Masuda et al. | |
| 2010/0057087 A1 | 3/2010 | Cha | |
| 2010/0121365 A1 | 5/2010 | O'Sullivan et al. | |
| 2010/0145341 A1 | 6/2010 | Ranck et al. | |
| 2010/0178631 A1 | 7/2010 | Gordils Wallis | |
| 2010/0286695 A1 | 11/2010 | Hannani | |
| 2011/0015634 A1 | 1/2011 | Smith | |
| 2011/0054884 A1 | 3/2011 | Drakwall | |
| 2011/0098710 A1 | 4/2011 | Spratt | |
| 2011/0112540 A1 | 5/2011 | Mclean | |
| 2011/0208194 A1 | 8/2011 | Steiner | |
| 2011/0238070 A1 | 9/2011 | Santangelo | |
| 2011/0238099 A1 | 9/2011 | Loreth | |

FOREIGN PATENT DOCUMENTS

| | | | |
|---|---|---|---|
| JP | 10263914 A * | 10/1998 | |
| JP | 2003291024 A * | 10/2003 | |
| WO | WO-2008061711 A2 | 5/2008 | |
| WO | WO-2008064350 A2 | 5/2008 | |
| WO | WO-2010061933 A1 | 6/2010 | |
| WO | WO-2011/023381 | 3/2011 | |
| WO | WO-2011132876 A2 | 10/2011 | |

OTHER PUBLICATIONS

Table of Contents, RedLine Tools catalog, www.redlinetools.com/images/PDFs/Redline09/RL062009_Sec1_Front%20p1-9_72.pdf, pp. 1-8.
Innovations 2005 catalog, Komet GEBR. BRASSELER GmbH & Co. KG, Lemgo, Germany, 28 pages.
Komet Burs mini catalogue 2007, Henry Schein Halas, www.henryschein.com.au, 19 pages.
Komet Surgery catalog, Mar. 2011, 8 pages.
Stryker Neuro Spine ENT brochure, Zyphr Burs, Kalamazoo, Michigan, www.stryker.com, 2011, 6 pages.
International Preliminary Report on Patentability and Written Opinion mailed Oct. 30, 2014 for PCT/US2013/036269, claiming priority to U.S. Appl. No. 13/447,372, filed Apr. 16, 2012.
Japanese Office Action mailed Nov. 10, 2015 for Japanese Application 2015-507064 claiming benefit of PCT/US2014/046827 claiming benefit of U.S. Appl. No. 13/944,650, filed Jul. 17, 2013.

* cited by examiner

SURGICAL BUR WITH NON-PAIRED FLUTES

FIELD OF THE INVENTION

This disclosure is directed to a surgical system for bone cutting or shaping and more particularly, to a surgical dissection tool of the surgical system.

BACKGROUND

During surgical procedures using cutting tools, surgeons often balance aggressiveness of cutting tools with the ability to precisely control the cutting tool. As a surgeon controls the cutting instruments to increase aggressiveness, potentially decreasing the time period of the surgical procedure, the surgeon may have less precise control. While non-aggressive cutting may be more precise, it may increase the time period of the surgical procedure.

A part of the reduced precision during aggressive cutting may be the result of tool chatter. Tool chatter may occur for several reasons. One reason is the spacing of the flutes. A cutting tool with "paired" flutes or an even number of flutes may chatter as a result of one cutting edge engaging tissue at the same time that another cutting edge is disengaging from tissue or may manifest when the cutting depth of multiple engaged flutes vary, producing asymmetric forces. In addition, tool chatter may result from an inability of tissue in the flutes to exit the flute before the flute reengages tissue. This may be compounded during aggressive cutting that can result in relatively large slices of tissue.

The present disclosure is directed to a surgical system for bone cutting or shaping addressing one or more of the limitations in the prior art.

SUMMARY OF THE INVENTION

In one exemplary aspect, the present disclosure is directed to a surgical dissection tool for cutting bone and other tissue. The dissection tool may include a distal end portion and a proximal end portion. A shank may extend between the distal end portion and the proximal end portion. A cutting head disposed at the distal end portion connects to the shank. It has an outer surface having an odd number of flutes formed therein. Each flute includes a rake surface intersecting with the outer surface to form a cutting edge, and a relief surface opposite the rake surface. The relief surface and the rake surface form a first angle. Each flute also includes a leading angled surface extending from the relief surface to a distal end portion of the cutting head, the leading angled surface and the rake surface forming a second angle substantially the same as the first angle.

In one aspect, the odd number of flutes comprises three flutes. In another aspect, the first and second angles are obtuse angles. In another aspect, the leading angled surface comprises one of a chamfer and a round. In another aspect, the flute further comprises a bevel between the leading angled surface and the rake surface.

In another exemplary aspect, the present disclosure is directed to a surgical dissection tool for cutting bone and other tissue that includes a shank and a cutting head connected to the shank. The cutting head and shank have a central longitudinal axis, and the cutting head has an outer surface having an odd number of flutes formed therein. Each flute may include a planar rake surface intersecting with the outer surface to form a cutting edge and may include a planar relief surface opposite the rake surface. The planar rake surface and the planar relief surface form an obtuse angle. A leading angled surface may extend from the planar relief surface to a distal end portion of the outer surface, and the leading angled surface of at least one of the flutes includes a distal-most end extending past the longitudinal axis.

In another exemplary aspect, the present disclosure is directed to a surgical dissection tool for cutting bone and other tissue that includes a shank and a cutting head connected to the shank. The cutting head and shank may have a central longitudinal axis and an outer surface. The outer surface may be substantially spherically shaped and may have three flutes formed therein. The outer surface between adjacent flutes of the three flutes forms an angle within a range of about 45-55 degrees. Each flute of the three flutes includes a planar rake surface intersecting with the outer surface to form a cutting edge. The planar rake surface is parallel to and offset from a reference plane through the longitudinal axis. Each flute also includes a planar relief surface opposite the rake surface and intersecting with the outer surface. The planar relief surface may extend to a proximal portion of the cutting head, the planar rake surface and the planar relief surface may form a first obtuse angle within a range of about 95 and 105 degrees. A leading angled surface may extend from the planar relief surface to a distal end portion of the outer surface. The leading angled surface and the planar relief surface may form a second angle substantially the same as the first obtuse angle. The leading angled surface of at least one of the three flutes may include a distal-most end extending past the longitudinal axis.

In another exemplary aspect, the present disclosure is directed to a surgical system having a surgical dissection cutter assembly with a surgical dissection tool as described herein.

BRIEF DESCRIPTION OF THE DRAWINGS

A more complete understanding of the present disclosure and advantages thereof may be acquired by referring to the following description taken in conjunction with the accompanying figures.

DETAILED DESCRIPTION

Reference is now made in detail to exemplary embodiments of the invention, examples of which are illustrated in the accompanying drawings. Wherever possible, the same reference numbers are used throughout the drawings to refer to the same or like parts.

The present disclosure is directed to a surgical dissection cutter assembly including a dissection tool driver that drives a surgical dissection tool during surgical procedures. The dissection tool may provide increased cutting control and cutting precision by reducing the incidence of chatter during cutting. This may permit a surgeon to make more aggressive dissections without compromising control and cutting precision. In turn, this may reduce the length of time required for some surgical procedures, benefitting the patient. In addition, reduced chatter may result in smoother cuts, which may increase healing and reduce recovery times.

The exemplary dissection tool disclosed herein is a surgical bur having non-paired flutes. As such, the flutes themselves are not spaced precisely 180 degrees apart. The offset flutes appear to provide a benefit of reduced chatter while still permitting relatively aggressive cutting. The advantage may derive from the offset in timing between the time one flute engages to cut tissue as another disengages the tissue during a single revolution of the dissection bur.

Figure 1:
FIG. 1 is an illustration of a surgical dissection cutter assembly according to the present invention use in a human patient.

FIG. 1 shows a human patient A undergoing a neurological operation. As is common practice, access to the brain or other neurological structures often requires delicate dissection of bone and other tissues to gain access. By way of example, a dissection cutter assembly employing a dissection tool driver 10 in accordance with one aspect of the present invention is shown being utilized to dissect a portion of patient A's bone and other tissue adjacent to the surgical access site.

Figure 2:
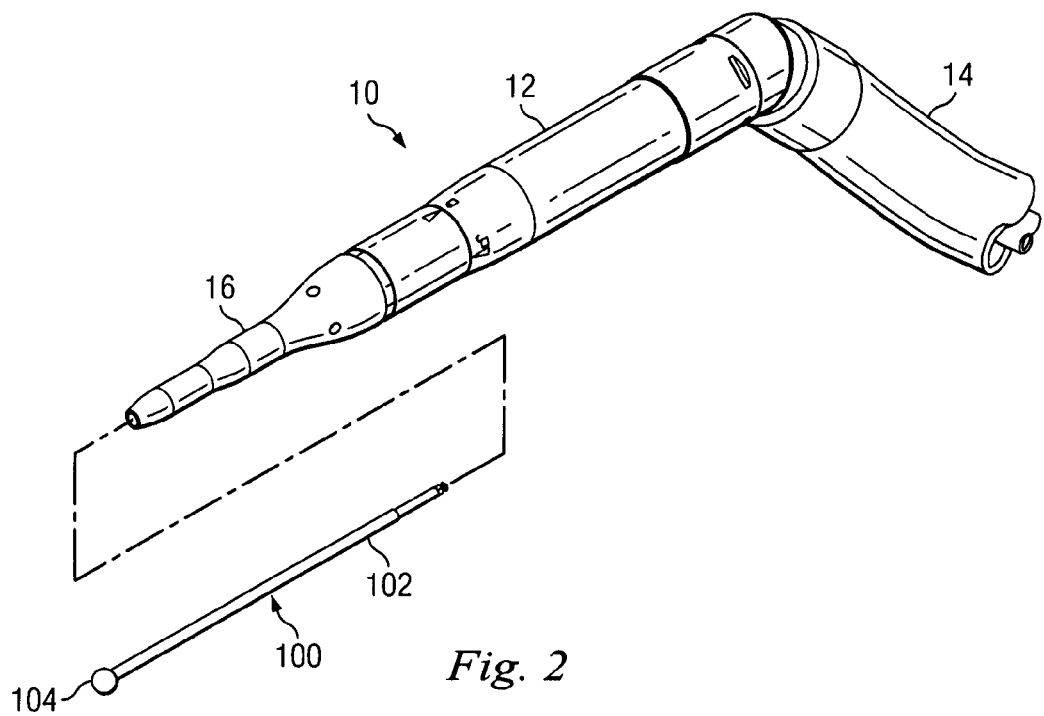
FIG. 2 is an illustration of partially exploded perspective view of a surgical dissection cutter assembly including a driver and a surgical dissection tool according to the present invention.

FIG. 2 illustrates the dissection tool driver 10 for the dissection of bone or other tissue in greater detail. The dissection tool driver 10 includes a motor housing 12, coupled to an air supply and hose assembly 14 that supplies pressurized air to a motor in the motor housing 12 and vents the low pressure exhaust air away from the surgical site. The dissection tool driver 10 further includes an attachment housing 16 that connects to a dissection tool 100. The dissection tool 100 is described in greater detail with reference to FIGS. 3-5.

Figure 3:
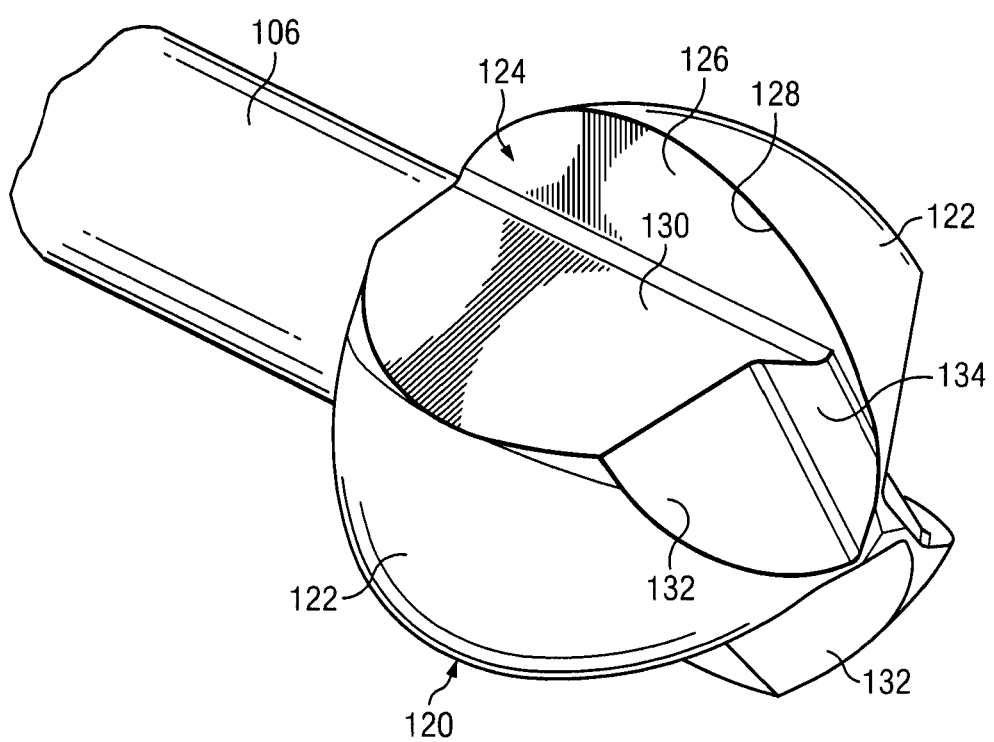
FIG. 3 is an illustration of an isometric view of a distal end of a surgical dissection tool according to one exemplary aspect of the present disclosure.
Figure 4:
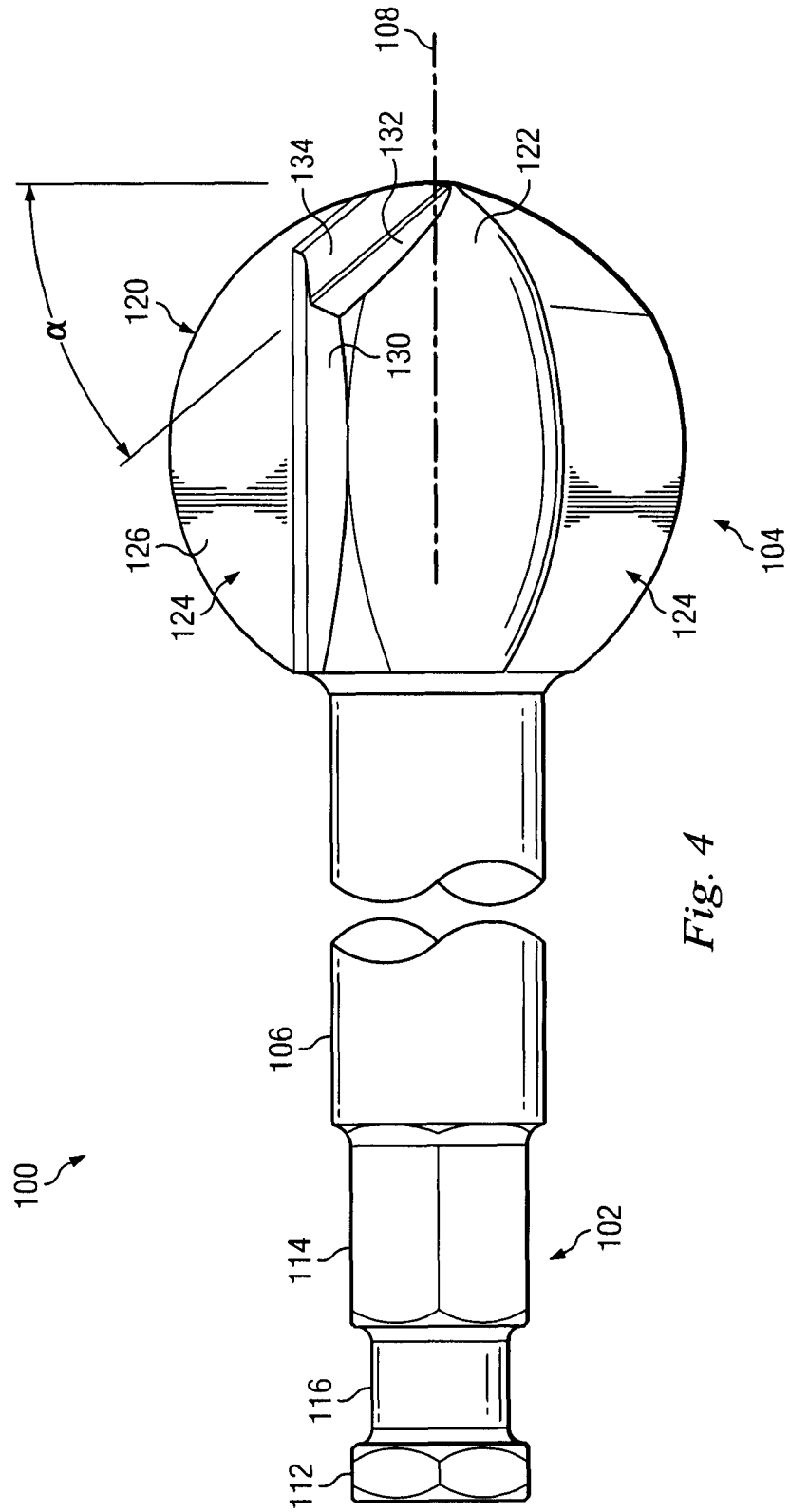
FIG. 4 is an illustration of a side view of a surgical dissection tool according to one exemplary aspect of the present disclosure.
Figure 5:
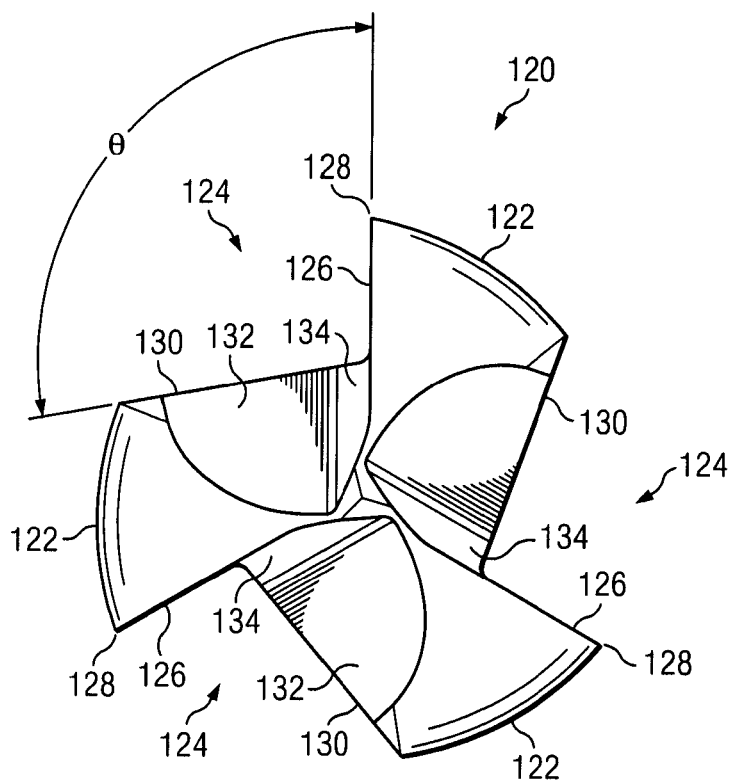
FIG. 5 is an illustration of an end view of a distal end of a surgical dissection tool according to one exemplary aspect of the present disclosure.

FIG. 3 shows an isometric view of a distal end portion, FIG. 4 shows a side view of the dissection tool 100, and FIG. 5 shows an end view of the distal end portion. Referring to these figures, the dissection tool 100 is, in this example, a surgical bur that includes a proximal end portion 102 and a distal end portion 104 connected by an extending shank or shaft 106.

The shank 106 has a longitudinal axis 108 defining a center-line of the proximal end portion 102 and the distal end portion 104. In one embodiment, the shank 106 includes a diameter within a range of about 0.030-0.150 inch.

The proximal end portion 102 is arranged to engage with and be driven by a shaft in the motor portion 12, but passes through and is supported by the attachment housing 16 in FIG. 2. In this example, the proximal end portion 102 includes a first non-circular region 112 when viewed in cross-section, a second non-circular region 114 when viewed in cross-section, and an intermediate region 116. In this example, the first and second non-circular regions 112, 114 are shown as hex-shaped surfaces and have the same cross-sectional shape. These regions are configured to engage with a driving portion of the dissection tool driver 10. The intermediate region 116 has a smaller cross-sectional area than the first and second non-circular regions 112, 114. It may be used to engage with or be engaged by the dissection tool driver 10 to anchor or otherwise secure the dissection tool 100 in the dissection tool driver 10. In this example, the intermediate region 116 is has a circular cross-section with a diameter smaller than the smallest cross-sectional width of the first non-circular region 112.

The distal end portion 104 includes a cutting head 120 connected to the shank 106. The transverse cross-section of the cutting head 120 is greater than the diameter of the shank 106. The cutting head 120 is shown as a surgical cutting bur with an outer surface 122. In this example, the outer surface 122 is substantially spherically shaped. In other embodiments, the cutting head 120 may have a cross-section smaller than at least a portion of the shank 106. In one embodiment, the shank 106 includes a neck with a curved or tapered surface that extends to the cutting head 120.

The cutting head 120 is formed with three symmetric cutting flutes 124 formed into the outer surface 122 and evenly spaced about the cutting head 120. Each cutting flute 124 includes a rake surface 126 forming a cutting edge 128 with the outer surface 122, and includes a relief surface 130 adjacent the rake surface 126. A distal region of the cutting head 120 includes a leading angled surface shown as a chamfer portion 132 leading to the relief surface 130. A bevel 134 connects the chamfer portion 132 to the rake surface 126. As can be seen, the cutting edge 120 forms a smooth arc from the distal-most portion of the spherical cutting head 120 to the proximal side of the cutting head 120.

In this example, the rake surface 126 is a planar surface across its length. Here, the rake surface 126 is offset from but parallel to a plane passing through the longitudinal axis 108. Accordingly, the rake surface 126 lies in a plane that does not intersect the center-line or longitudinal axis 108 of the dissection tool 100. While shown as being offset after the centerline, in other embodiments, the rake surface 126 is offset from but parallel to a plane before or in front of a plane passing through the longitudinal axis to impart a desired rake angle. In one embodiment the rake surface is disposed so that a plane through the rake angle intersects the axis for a neutral rake angle. Although shown as planar, in other embodiments, the rake surface 126 surface is angled or formed by a helix.

The relief surface 130 forms the opposing side of the flute 124 and, together with the rake surface 126, forms an angle θ within a range of about 85-120 degrees, although additional angles are contemplated. In one embodiment, the angle θ is within a range of about 95-105 degrees and in another embodiment, the angle is about 100 degrees. The relief surface extends from the chamfer portion 132 to a proximal portion of the cutting head 120. Different embodiments of the dissection tool 100 include angles between the rake surface 126 and the relief surface 130 that are acute, right or obtuse. In some embodiments, the angle θ is within the range of about 90° and 100°.

As best seen in FIG. 4, the chamfer portion 132 angles from the relief surface 130 to a distal end of the cutting head 120. In the example shown, the chamfer portion 132 is cut at an angle a measured from a line traverse to the axis 108 to fall between about 20 and 70 degrees. In one example, the chamfer portion 132 is formed with an angle α between the range of about 35-45 degrees, and in one example, the angle α is about 40 degrees. The angle α is formed so that the end of the chamfer portion 132 extends past the centerline or axis 108, as can be seen in FIG. 4. In addition, in the embodiment shown, the chamfer portion 132 is formed relative to the rake surface 126 to form an angle that substantially corresponds to the angle θ0 formed between the relief surface 130 and the rake surface 126.

FIG. 5 shows how the bevel 134 intersects with the outer surface 122 of the cutting head 120 to form a leading surface with the outer surface 122 at the distal most end of the cutting head. The bevel 134 angles the cutting edge 128 so that each flute 124 is independent of and does not intersect the other flutes, even though they each extend past the centerline or axis 108. In the embodiment shown, the cutting head 120, albeit spherically shaped, includes a truncated proximal end that is brazed to the shank 106.

Figure 6:
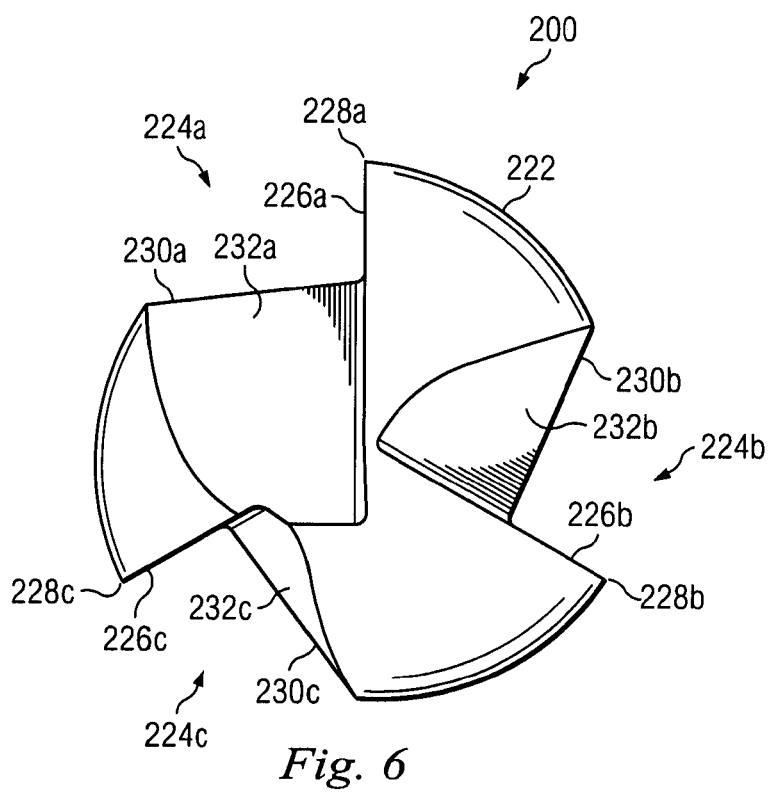
FIG. 6 is an illustration of a side view of a distal end of a surgical dissection tool according to one exemplary aspect of the present disclosure.
Figure 7:
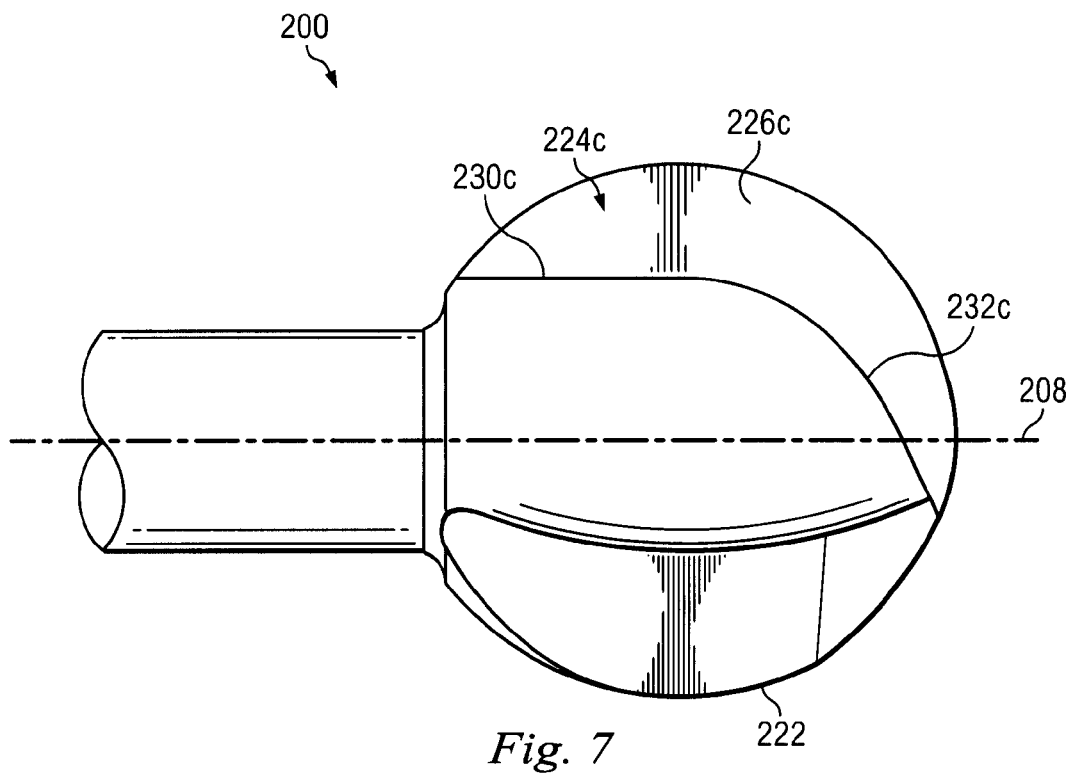
FIG. 7 is an illustration of another side view of a distal end of a surgical dissection tool of FIG. 6, rotated from the position in FIG. 6 according to one exemplary aspect of the present disclosure.
Figure 8:
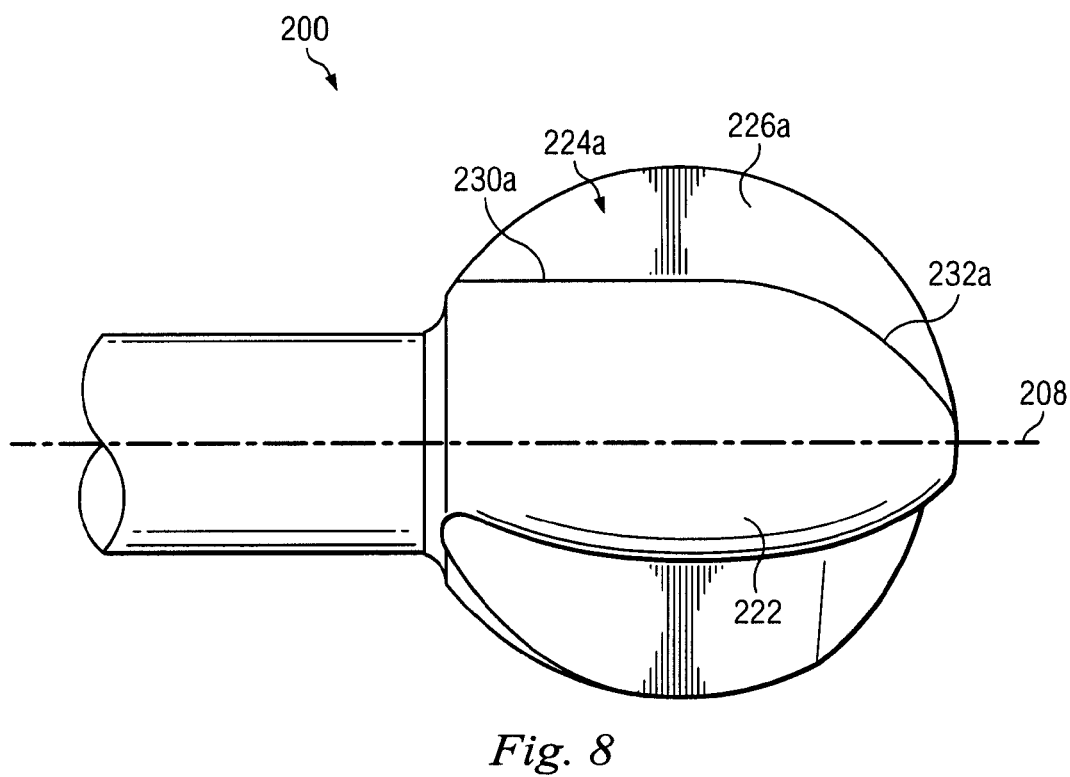
FIG. 8 is an illustration of an end view of a distal end of a surgical dissection tool according to one exemplary aspect of the present disclosure.
Figure 9:
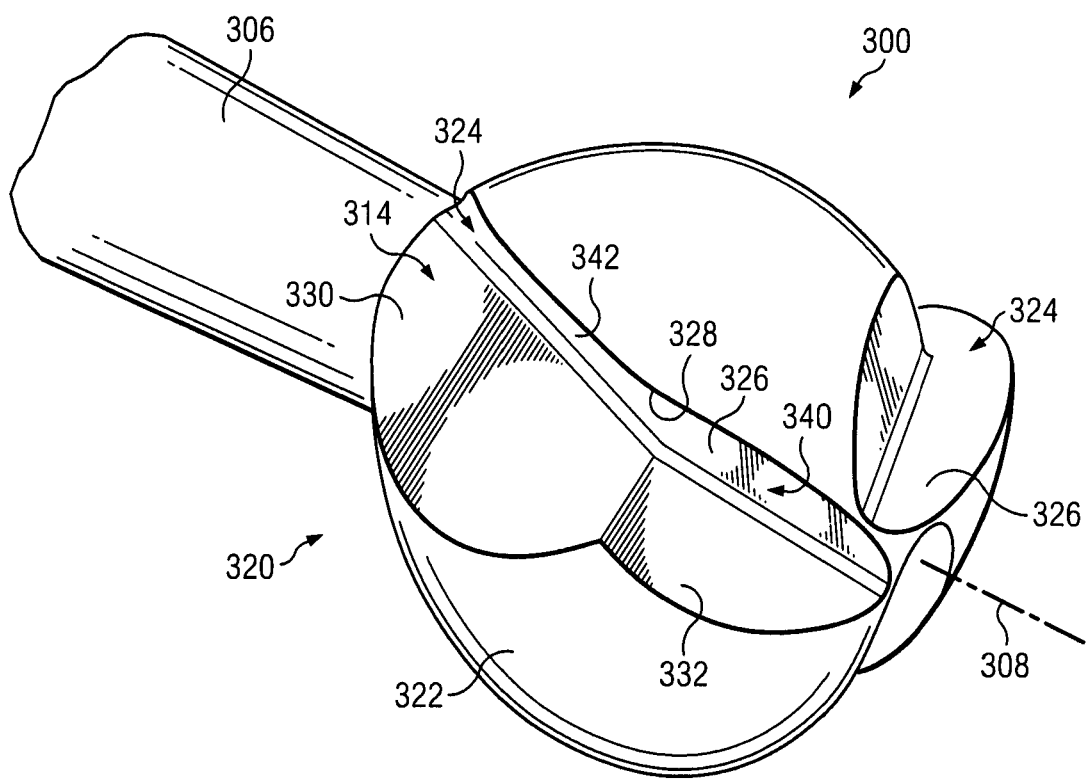
FIG. 9 is an illustration of an isometric view of a distal end of a surgical dissection tool according to another exemplary aspect of the present disclosure.

FIGS. 6-8 show an additional embodiment of a dissection tool, referenced here by the numeral 200. Some of the sizes, angles, and shapes of features of the dissection tool 200 are similar to those described above, and will not be repeated here. The dissection tool 200 includes a shank 206 and a proximal end similar to the shank and proximal end discussed above with reference to the dissection tool 100. Therefore, these will not be described further here.

The dissection tool 200 includes a cutting head 220 with a spherical outer surface 222 having three cutting flutes 224a-c formed therein, with each cutting flute 224a-c having a respective planar rake surface 226a-c that intersects the outer surface 222 to form a respective cutting edge 228a-c. A relief surface 230a-c forms an opposing wall to each respective rake surface 226a-c of each cutting flute 224a-c. As described above, in one embodiment, the rake surfaces 226 are parallel to, but offset from a plane through the centerline or axis 208. In other embodiments, the rake surfaces 226 form planes that pass through the centerline or axis 208.

Instead of having identical flutes as disclosed with reference to the dissection tool 100, the dissection tool 200 includes cutting flutes that vary from each other. In this example, each cutting flute 224a-c includes a respective leading angled surface shown as a chamfer or a round 232a-c extending from its most distal end to the relief surface 230. The chamfers or rounds 232a-c of each flute 224a-c, however, have different depths or curvatures. This can be understood with reference to FIG. 6 where each chamfer or round is different sized.

FIGS. 7 and 8 each show an illustration of a side view of the cutting head 220 showing the curvature along the different flutes of the dissection tool 200. FIG. 7 shows the profile of the relief surface 230c and the chamfer or round 232c. FIG. 8 shows the profile of the relief surface 230a and the chamfer or round 232a. As can be seen by comparison, the chamfer or round 232a in FIG. 8 is substantially larger than the chamfer or round 232c in FIG. 7. As can be seen in FIG. 8, the leading angled surface comprises both a chamfer and a round. The round connects the chamfer and the relief surface 230a. Furthermore, the rake surface 228 continues the full length of the relief surface 230 and the chamfer or round 232. That is, the dissection tool 200 does not include a bevel surface. However, since the chamfer or round 232 varies by flute in the exemplary tool 200, the surface area of the rake surface also varies from flute to flute. As can be seen by comparing FIGS. 7 and 8, the area of the rake surface 226a is greater than the area of the rake surface 226c. Similarly, the length of the cutting edge varies from flute to flute, and the cutting edge 228a is greater than that of the cutting edge 228c. In addition, chamfer or round 232a in the cutting flute 224a extends past the centerline or axis 208 as shown in FIG. 8, while the cutting flutes 224b and 224c do not extend past the centerline or axis 208.

FIGS. 9-12 show an additional embodiment of a dissection tool, referenced here by the numeral 300. Some of the sizes, angles, and shapes of features of the dissection tool 300 are similar to those described above, and will not be repeated here. The dissection tool 300 includes a shank 306 and a proximal end similar to the shanks and proximal ends discussed above.

The dissection tool 300 includes a cutting head 320 with an outer surface 322 having three cutting flutes 324 formed therein, with each cutting flute 324 having a respective rake surface 326 that intersects the outer surface 322 to form a respective cutting edge 328. Here, the cutting flutes 324 are substantially identically shaped and therefore, are all referred to by the same reference numeral.

In this embodiment, the rake surface 326 is helix shaped, with a leading portion 340 and a trailing portion 342. The helix angle increases the effective shearing action thus reducing cutting forces and the amount of heat generated during the bone cutting process. Chip ejection also may be improved. During cutting, as the bur rotates about the longitudinal axis 308, the leading portion 340 is the first portion to engage the bone tissue during a cutting action and the trailing portion 342 follows the leading portion 340. This may provide additional stability during cutting to the three-flute bur because resistance from the bone tissue is applied through a progressive siding action. This makes the cutting forces more constant with less chance for chatter. Instead of the whole cutting edge of a flute engaging the bone at once, the helix makes the leading portion 340 engage the bone first, and the remainder of the cutting edge engages bone over a very short period of time. This reduces both vibration and dampening, resulting in greater levels of stability.

Figure 12:
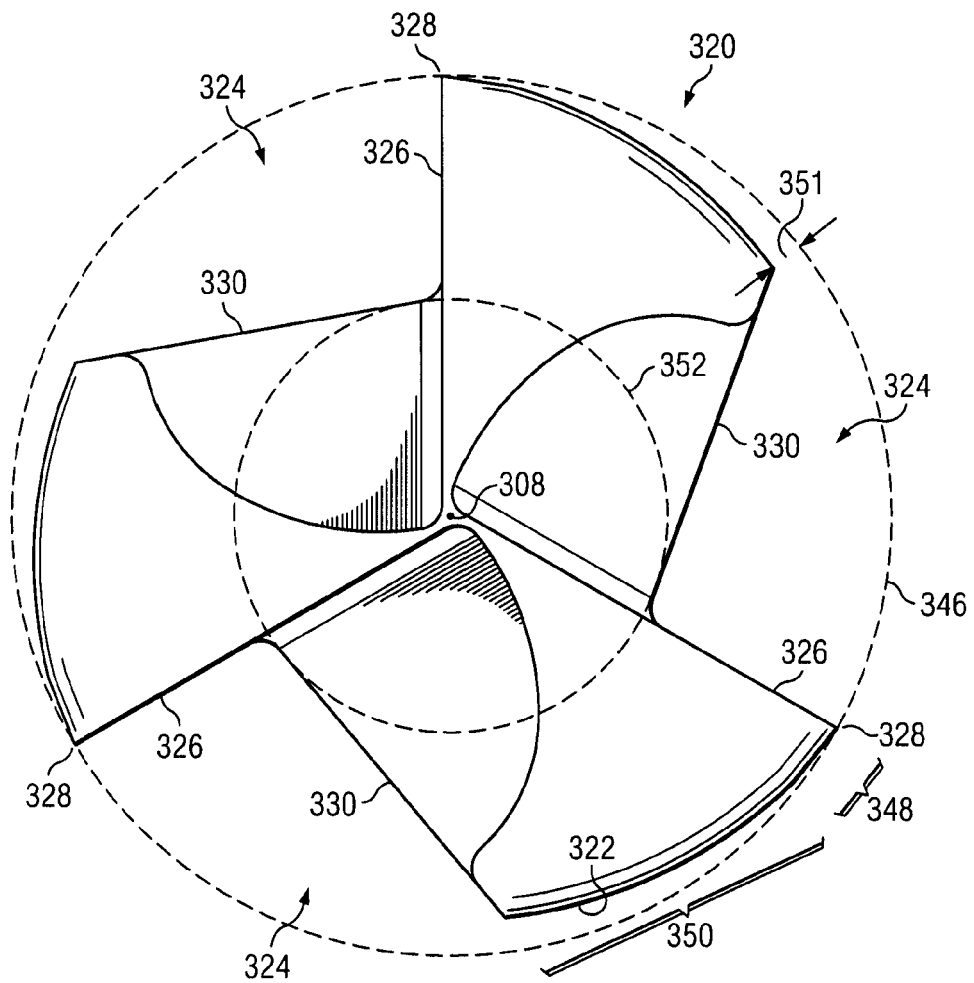
FIG. 12 is an illustration of an end view of a distal end of a surgical dissection tool according to one exemplary aspect of the present disclosure.

In this embodiment, the leading portions 340 of the respective rake surfaces 326 are parallel to, but offset from a front of a plane through the centerline or axis 308. In other embodiments, the leading portions 340 of the rake surfaces 326 form planes that pass through the centerline or axis 308 or that are behind a plane through a centerline or axis 308. As can be seen in FIG. 12, the leading edge extends in front of and past the centerpoint.

FIG. 12 shows an end view of the dissection tool 300 with a reference boundary 346 creating a circle that intersects the cutting edges 328 of the dissection tool 300. Although shown in cross-section as a line, in one example, the reference boundary 346 is a spherical boundary interesting the cutting edges 328. The cutting edges 328 of the dissection tool 300 intersect with the spherical reference boundary 346. However, in cross-section, the outer surface 322 gradually tapers inwardly from the reference boundary 346. As can be seen in FIG. 12, the outer surface 322 includes a tapered portion 348 followed by a curved portion 350. The tapered portion 348 extends from the cutting edge rearward along the outer surface 322. The tapered portion 348 is followed by a curved portion 350 that is formed with a changing radius as an Archimedes spiral or a cam surface. The cam relief formed as a result of the tapers portion and the curved portion 350 is labeled with the reference numeral 351. This provides the greatest clearance permitting the bur to advance into the bone tissue without excessive interference from the outer surface 322 engaging the newly cut surface. This can help reduce heating that may occur if the outer surface were to be engaged with or rubbing on the bone tissue.

A relief surface 330 forms an opposing wall to each respective rake surface 326 of each cutting flute 324. In the embodiment of the dissection tool 300, the flutes 324 are all substantially identical, and are similar to the rake surfaces described above. A reference line 352 identifies a web thickness of the cutting head 320. The web thickness is the minimum diameter of the solid portion of the cutting head. When using three flutes as shown in FIG. 12, the web thickness has a radius equal to about half of the radius to the cutting edges 328. Other embodiments have a web thickness that is either higher and lower. In one embodiment, the web thickness radius is within a range of about 40% to 80% of the radius to the cutting edges 328.

Figure 10:
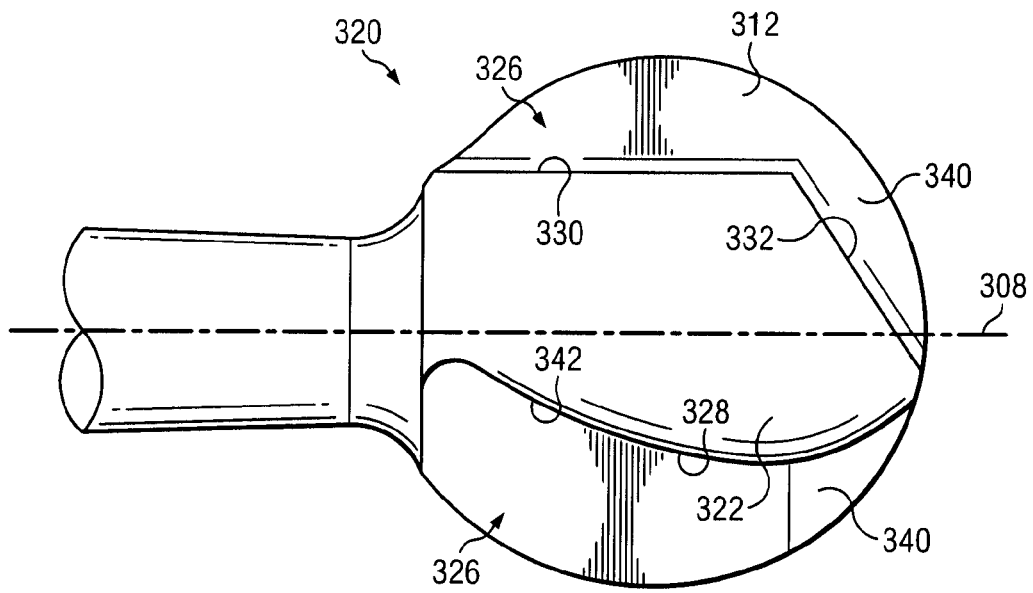
FIG. 10 is an illustration of a side view of a surgical dissection tool according to one exemplary aspect of the present disclosure.
Figure 11:
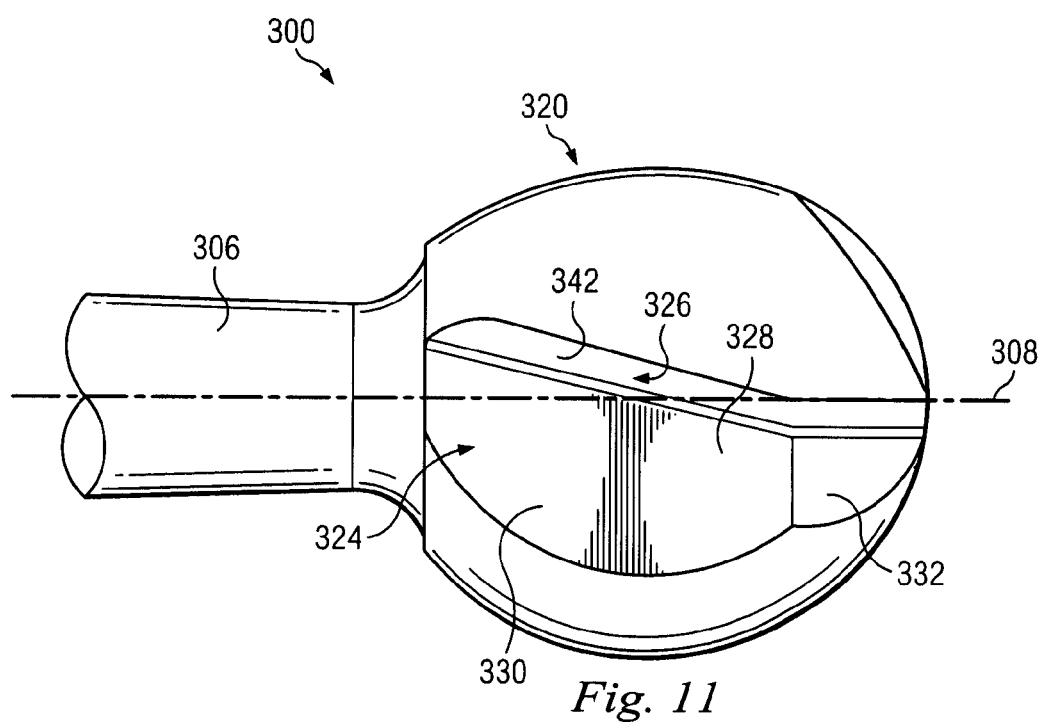
FIG. 11 is an illustration of another side view of a surgical dissection tool according to one exemplary aspect of the present disclosure, rotated from the side view shown in FIG. 10.

FIGS. 10-11 each show an illustration of a side view of the cutting head 320 showing the curvature along the different flutes of the dissection tool 300. FIG. 10 shows the profile of the relief surface 330c and the chamfer or round 332c. FIG. 11 shows the profile of the rake surface 326 and the cutting edge 328. As can be seen by comparison, the rake surface 328 forms a helix that extends from the leading portion 340 to the trailing portion 342.

Figure 13:
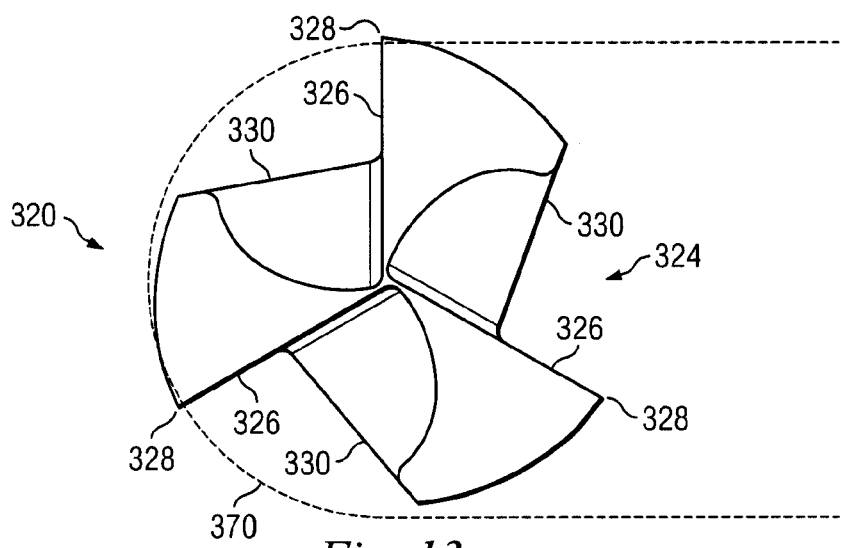
FIG. 13 is an illustration of an end view of a distal end of a surgical dissection tool as it relates to bone tissue cutting a path in the tissue according to one exemplary aspect of the present disclosure.

FIG. 13 shows the exemplary surgical dissection tool 300 in a cutting environment. In this view, a bottom view of the cutting tool 300 cuts a path in bone tissue structure 370, with the bone tissue structure 370 being transparent in order to display the cutting tool.

In FIG. 13, the cutting edge 328 of the dissection tool 300 is shown engaged in and cutting material from the bone structure 370. The cutting edge 328 is also just engaging into the bone structure 370. As can be seen, at this point in time, there are only two cutting edges 328 engaged in the bone structure 370. The third cutting edge 328 moved out of engagement with the bone structure. Because the flutes are offset and not directly across from each other, the cutting edge 328 moves out of contact with the bone structure before the cutting edge 328 engages the bone structure. The time differential between the time one cutting edge engages tissue and a separate cutting edge disengages the tissue during a single revolution of the dissection bur may provide advantages in decreased chatter. Accordingly, at any single point in time, only two out of the three cutting edges are in contact with the bone structure.

Although the exemplary dissection tools are burs with three flutes, the dissection tools may have additional non-paired flutes. For example, one example of the dissection tool includes five flutes. In use, the odd number of flutes may result in a reduced level of chatter during bone or cutting. Since cutting occurs by rotating the dissection tool about its longitudinal axis, the odd number of flutes offsets the timing of initial cutting edge engagement and cutting edge disengagement. This offset in timing is thought to reduce the incidence of chatter while still permitting aggressive cutting action. Furthermore, since at least one of the flutes has a cutting edge that extends past the longitudinal axis or centerline, the angle that the cutter is held at by the surgeon is not as critical as it might otherwise be.

It is evident that the particular illustrative embodiments disclosed above may be altered or modified and all such variations are considered within the scope and spirit of the present invention.

We claim:

1. A surgical dissection tool for cutting bone and other tissue, comprising:
    a distal end portion;
    a proximal end portion;
    a shank extending between the distal end portion and the proximal end portion,
    a cutting head at the distal end portion connected to the shank, the cutting head having a spherical outer surface, the outer surface having an odd number of flutes formed therein, each flute comprising:
        a planar rake surface intersecting with the spherical outer surface to form a cutting edge, the planar rake surface is parallel to and offset from a reference plane through a longitudinal axis of the cutting head;
        a relief surface opposite the rake surface, the relief surface and the rake surface forming a first angle; and
        a leading angled surface extending from the relief surface to a distal end portion of the cutting head, the leading angled surface and the rake surface forming a second angle substantially the same as the first angle.

2. The surgical dissection tool of claim 1, wherein the odd number of flutes consists of three flutes.

3. The surgical dissection tool of claim 1, wherein the first and second angles are obtuse angles, and wherein the relief surface extends to a proximal end of the cutting head.

4. The surgical dissection tool of claim 1, wherein the leading angled surface comprises one of a chamfer and a round.

5. The surgical dissection tool of claim 1, wherein the flute further comprises a bevel between the leading angled surface and the rake surface.

6. The surgical dissection tool of claim 5, wherein the flute further comprises a bevel between the leading angled surface and the distal end portion of the outer surface.

7. The surgical dissection tool of claim 1, wherein each of the flutes is substantially identical.

8. A surgical dissection tool for cutting bone and other tissue, comprising:
    a shank;
    a cutting head connected to the shank, the cutting head and shank having a central longitudinal axis and having a spherical outer surface with an odd number of flutes formed therein, each flute comprising:
        a planar rake surface intersecting with the spherical outer surface to form a cutting edge, the planar rake surface is parallel to and offset from a reference plane through the longitudinal axis;
        a planar relief surface opposite the rake surface, the planar rake surface and the planar relief surface forming an obtuse angle; and
        a leading angled surface extending from the planar relief surface to a distal end portion of the outer surface,
    wherein the leading angled surface of at least one of the flutes includes a distal-most end extending past the longitudinal axis.

9. The surgical dissection tool of claim 8, wherein the odd number of flutes consists of three flutes.

10. The surgical dissection tool of claim 8, wherein the first and second angles are obtuse angles, and wherein the relief surface extends to a proximal end of the cutting head.

11. The surgical dissection tool of claim 8, wherein the leading angled surface comprises one of a chamfer and a round.

12. The surgical dissection tool of claim 8, wherein each flute further comprises a bevel between the leading angled surface and the rake surface, the bevel disposed between the leading angled surface and the distal end portion of the outer surface.

13. The surgical dissection tool of claim 8, wherein the planar rake surface is a planar portion and the rake surface comprises a helix.

14. A surgical dissection tool for cutting bone and other tissue, comprising:
   a shank; and
   a cutting head connected to the shank, the cutting head and shank having a central longitudinal axis and an outer surface, the outer surface having only three flutes formed therein, wherein a spherically shaped outer surface between adjacent flutes of the three flutes forms an angle within a range of about 45-55 degrees, each flute of the three flutes comprising:
      a planar rake surface intersecting with the outer surface to form a cutting edge, the cutting edge of three flutes being disposed to define a substantially spherically shaped reference boundary, wherein the planar rake surface is parallel to and offset from a reference plane through the longitudinal axis;
      a planar relief surface opposite the rake surface and intersecting with the outer surface, the planar relief surface extending to a proximal portion of the cutting head, the planar rake surface and the planar relief surface forming a first obtuse angle within a range of about 95 and 105 degrees; and
      a leading angled surface extending from the planar relief surface to a distal end portion of the outer surface, the leading angled surface and the planar relief surface forming a second angle at substantially the same angle as the first obtuse angle, wherein the leading angled surface of at least one of the three flutes includes a distal-most end extending past the longitudinal axis.

15. The surgical dissection tool of claim 14, wherein each of the three flutes is substantially identical.

* * * * *